United States Patent [19]

Molina y Vedia et al.

[11] Patent Number: 5,683,675
[45] Date of Patent: Nov. 4, 1997

[54] METHOD OF TREATING RETAINED PULMONARY SECRETIONS

[75] Inventors: Luis Miguel Molina y Vedia; Monroe Jackson Stutts; Richard C. Boucher, Jr.; David C. Henke, all of Chapel Hill, N.C.

[73] Assignee: Molichem Medicines, Inc., Chapel Hill, N.C.

[21] Appl. No.: 433,872

[22] Filed: May 2, 1995

Related U.S. Application Data

[62] Division of Ser. No. 74,315, Jun. 9, 1993, Pat. No. 5,512,267.

[51] Int. Cl.$^6$ ........................................... A61K 9/12
[52] U.S. Cl. ................... 424/45; 424/46; 514/924
[58] Field of Search ..................... 424/45, 46; 514/924

[56] References Cited

U.S. PATENT DOCUMENTS 5,135,910  8/1992  Blackburn et al. ............... 514/2

FOREIGN PATENT DOCUMENTS 09739  9/1990  WIPO .

OTHER PUBLICATIONS

Mattick, A.T.R., et al. (1947). *Lancet*, vol. ii, pp. 5–7.
Berkow, R. (1992). The Merck Manual, 16th. edition. Merck & Co., Inc., pp. 139–146; pp. 2045–2047.

*Primary Examiner*—Raj Bawa
*Attorney, Agent, or Firm*—Myers, Bigel, Sibley & Sajovec

[57] ABSTRACT

A method of facilitating the clearance of retained pulmonary secretions in a subject using lantibiotics is disclosed. The method comprises administering to the lungs of the subject an effective amount of a lantibiotic. The lantibiotic is preferably administered by topically applying it to the respiratory epithelia, such as by generating an aerosol thereof which is then inhaled by the subject. A preferred lantibiotic for carrying out the present invention is duramycin. The method may be used in treating disorders such as cystic fibrosis, chronic bronchitis, and asthma. Also disclosed is a method of combatting tuberculosis comprising administering a lantibiotic to a subject in need of such treatment.

7 Claims, 8 Drawing Sheets

METHOD OF TREATING RETAINED PULMONARY SECRETIONS

This application is a division of prior application Ser. No. 08/074,315, filed Jun. 09, 1993, now U.S. Pat. No. 5,512,267 issued on Apr. 30, 1996, the disclosure of which is incorporated by reference herein in its entirety.

FIELD OF THE INVENTION

The present invention relates to a method of removing retained mucus secretions from the lungs of a subject by administering a lantibiotic such as duramycin to the lungs of the subject. The present invention also relates to a method of combatting infection by *Mycobacterium tuberculosis*.

BACKGROUND OF THE INVENTION

In cystic fibrosis several functions of airway epithelia are abnormal, and deficiencies in both $Cl^-$ transport and $Na^+$ absorption are well documented. See, e.g. Knowles et al., *Science* 221, 1067 (1983); Knowles et al., *J. Clin. Invest.* 71, 1410 (1983). It is believed that impaired chloride secretion is one of the causes of the thickened airway surface liquid that characterizes cystic fibrosis. This thickened airway fluid contributes to the recurrent pulmonary infections and loss of ventilatory function that occur in cystic fibrosis. Retained airway secretions are also known to contribute to the morbidity of other pulmonary diseases such as asthma and chronic obstructive pulmonary disease.

The therapeutic goal in cystic fibrosis and other pulmonary diseases in which the water content of the mucus is altered is to remove retained secretions from the lungs. For example, the use of aerosolized amiloride to facilitate the removal of retained mucus secretions is described in U.S. Pat. No. 4,501,729. Amiloride appears to block $Na^+$ reabsorption by airway epithelial cells, and therefore inhibits water absorption from mucus.

A different therapeutic approach is to increase the water content of the airway surface liquid by modulating the activity of chloride channels. An example of this is the administration of ATP or UTP, which appear to induce hydrated mucus secretions by stimulating chloride secretion from respiratory epithelial cells. See, e.g., C. Stock, Breathing Easier: A Promising Treatment for Cystic Fibrosis, *Endeavors*, 10, 10–11 (Fall 1992) (Published by the Office of Research Services, The University of North Carolina at Chapel Hill).

Tuberculosis, while also primarily involving the lungs of afflicted subjects, is an infectious disease caused by the bacteria *Mycobacterium tuberculosis*. While most commonly occurring in the lungs, tuberculosis infections may occur anywhere in the body and may be widely disseminated. The development of streptomycin in 1944, isoniazid (INH) in 1952, ethambutol in 1952, and rifampin in 1972 led to a decreasing prevalence of tuberculosis up until approximately 1985, when the number of reported cases began to increase, Bloom and Murray *Science*, 257, 1055 (1992). Outbreaks of multi-drug resistant (MDR) tuberculosis are occurring with increasing frequency, and pose a major public health problem, *Morbidity and Mortality Weekly Report*, 41, 5 (1992). Tuberculosis remains the leading cause of death in the world from a single infectious disease.

SUMMARY OF THE INVENTION

A method of facilitating lung mucus clearance in a subject in need of such treatment is disclosed. The method comprises administering to the lungs of the subject a lantibiotic such as duramycin or a pharmaceutically acceptable salt thereof (hereinafter referred to as an "active compound"), in an amount effective to facilitate clearance of lung mucus. The lantibiotic is preferably administered to the lungs by topically applying the lantibiotic to the respiratory epithelia (e.g., the nasal epithelia, trachea, and bronchi).

The method of the present invention may further comprise the step of concurrently administering a sodium channel blocker such as amiloride to the subject in an amount effective to inhibit the reabsorption of water from lung mucous secretions.

The method of the present invention may also further comprise the step of removing retained mucus secretions from the lungs of the subject prior to the step of administering the lantibiotic so that application of the active agent to the respiratory epithelia is facilitated. Alternatively, the present invention may be carried out prophylactically on patients such as children afflicted with cystic fibrosis prior to substantial airway blockage and decline of respiratory function.

A method of combatting cystic fibrosis in a subject in need of such treatment by administering a lantibiotic as given above to said subject in an amount effective to hydrate lung mucus secretions is one particular aspect of the foregoing method.

A method of combatting chronic bronchitis in a subject in need of such treatment by administering a lantibiotic as given above to said subject in an amount effective to hydrate lung mucus secretions is another particular aspect of the foregoing.

A method of combatting asthma in a subject in need of such treatment by administering a lantibiotic as given above to said subject in an amount effective to hydrate lung mucus secretions is still another more particular aspect of the foregoing.

A second aspect of the present invention is a pharmaceutical composition containing an active compound as disclosed herein, in an amount effective to facilitate the clearance of lung mucous secretions, in a pharmaceutically acceptable carrier (e.g., a sterile liquid or solid carrier comprised of respirable particles). The pharmaceutical composition may further contain a sodium channel blocker such as amiloride in an amount effective to inhibit the reabsorption of water from lung mucous secretions.

A third aspect of the present invention is the use of an active compound as disclosed herein for the manufacture of a medicament for the prophylactic or therapeutic clearance of lung mucous secretions in a patient in need of such treatment.

The use of an active compound as disclosed herein for the manufacture of a medicament for the prophylactic or therapeutic treatment of cystic fibrosis in a subject in need of such treatment is a particular aspect of the foregoing.

The use of an active compound as disclosed herein for the manufacture of a medicament for the prophylactic or therapeutic treatment of chronic bronchitis in a subject in need of such treatment is another particular aspect of the foregoing.

The use of an active compound as disclosed herein for the manufacture of a medicament for the prophylactic or therapeutic treatment of asthma in a subject in need of such treatment is still another particular aspect of the foregoing.

A fourth aspect of the present invention is a method of treating *Mycobacterium tuberculosis* infection, particularly drug resistant tuberculosis infections, in a subject in need of such treatment. The method comprises administering to the subject a lantibiotic such as duramycin or a pharmaceutically acceptable salt thereof in an amount effective to combat *M. tuberculosis* infections. The method may further comprise the step of concurrently administering additional anti-tubercular agents in amounts effective to combat *M. tuberculosis* infections.

A fifth aspect of the present invention is a pharmaceutical composition containing an active compound as disclosed herein, in an amount effective to combat *M. tuberculosis* infections, in a pharmaceutically acceptable carrier. The pharmaceutical composition may further contain additional anti-tuberculosis agents in amounts effective to combat *M. tuberculosis* infections.

A sixth aspect of the present invention is the of an active compound as disclosed herein for the manufacture of a medicament for the prophylactic or therapeutic treatment of *M. tuberculosis* infection in a patient in need of such treatment.

Duramycin (also known as PA48009) is one of a group of lanthionine-containing polypeptide antibiotics. Lanthionine-containing polypeptides are also known as lantibiotics. See generally G. Jung, *Angew. Chem. Int. Ed. Engl.* 30, 1051–1068 (1991). The ability of duramycin to increase chloride secretion has been reported. Stone et al., *J. Biol. Chem.* 259, 2701 (1984); Cloutier et al., *Pediatr. Pulmonol.* 2(Suppl), 112 (1987); Cloutier et al., *Pediatr. Pulmonol.* 2(Suppl), 99 (1988); Cloutier et al., *Pediatr. Pulmonol.* 4(Suppl), 116 (1989); Cloutier et al., *Am. J. Physiol.*, 259, C450 (1990). The use of duramycin for facilitating the removal of retained pulmonary mucus secretions has not heretofore been suggested. See M. Roberts et al., *J. Pharm. Exp. Ther.* 259, 1050, 1058 (1991) ("It seems unlikeley, therefore, that the nonspecific effects of duramycin on animal cells can serve in useful therapeutic strategies.").

DETAILED DESCRIPTION OF THE INVENTION

Figure 1:
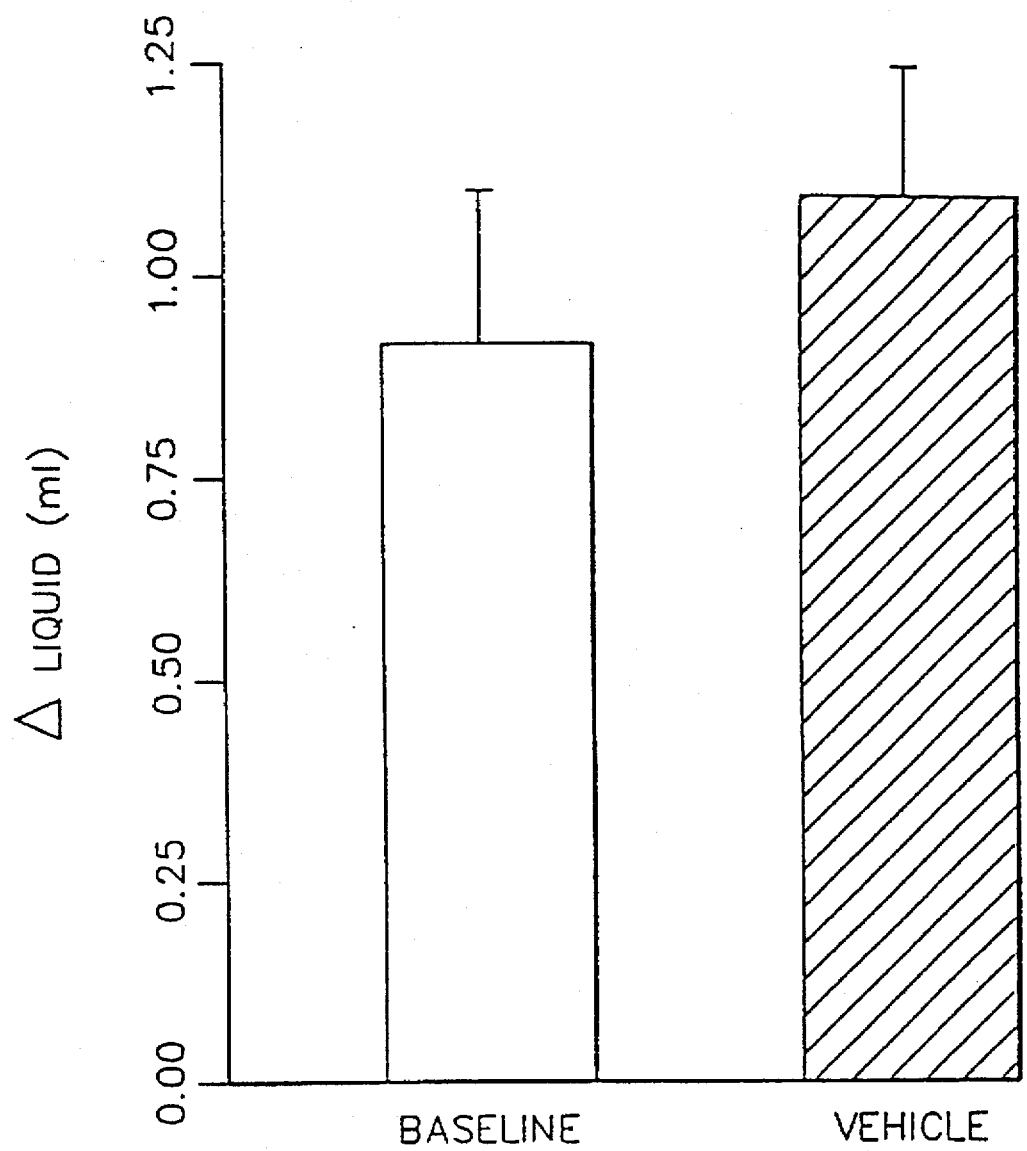
FIG. 1 is a graph comparing the amount of liquid recovered from the trachea in a canine model at baseline (open box) and that recovered after nebulization of normal saline vehicle (cross-hatched box).

The method of the present invention can be used to facilitate (i.e., enhance, speed, assist) the clearance of mucus secretions from the lungs of a subject in need of such treatment for any reason, including (but not limited to) retained secretions arising from airway diseases such as cystic fibrosis, chronic bronchitis, asthma, bronchiectasis, and post-operative atelectasis (plugging of airways with retained secretions after surgery).

While applicants do not wish to be bound to any particular theory of the instant invention, it appears that the clearance of lung mucus secretions is facilitated in the instant invention by the hydrating of the lung mucous secretions, with removal of the secretions by mucociliary action then being facilitated.

The present invention is concerned primarily with the treatment of human subjects but may also be employed for the treatment of other mammalian subjects, such as dogs and cats, for veterinary purposes.

Lantibiotics include, but are not limited to, duramycin, nisin, subtilin (Gross et al. *Z. Physiol. Chem.*, 354, 810 (1973)), epidermin (Schnell et al. *Nature*, 333, 276 (1988)), Pep 5 (Sahl, *J. Bacteriol.*, 162, 833 (1985)), gallidermin (Kellner et al, *Eur. J. Biochem.* 177, 53 (1988)), mersacidin, actagardine (Kettenring et al., *J. Antibiotics*, 53, 1082 (1990) ), cinnamycin (Kessler et al., *Helv. Chim. Acta,* 71, 1924 (1988)), duramycin, and ancovenin (Wakamiya et al., *Tetrahedron Lett.* 26, 665 (1985)). These compounds are known or can be made in accordance with known procedures which will be apparent to those skilled in the art.

The structure of duramycin is known. See Hayashi et al., *J. Antibiotics*, 43, 1421 (1990). Duramycin is available from Sigma Chemical Co. (St. Louis, Mo., U.S.A.) as catalog no. D3168, or can be produced in accordance with known techniques from *Streptoverticillium cinnamoneum* subsp. *azacolutum* (NRRL B-1699) (available from the USDA Agricultural Research Service, Peoria, Ill., U.S.A.) in accordance with known techniques. See, e.g., Hayashi et al., supra, Pridham et al., *Phytopathology* 46, 575–581 (1956); Shotwell et al., *J. Am. Chem. Soc.* 80, 3912 (1958); S. Nakamura et al. *Biochem.* 23, 385 (1984).

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

In one embodiment of the present invention, aerosolized duramycin in solution is administered to the lungs of a subject in an amount sufficient to achieve dissolved concentrations of duramycin on the airway surfaces of the subject of from $10^{-8}$ Moles/liter to $10^{-5}$ Moles/liter. More preferably, the dosage may be an amount sufficient to achieve dissolved concentrations of duramycin on the airway surfaces of the subject of about $10^{-7}$ Moles/liter to $10^{-6}$ Moles/liter.

Sodium channel blockers which may be used in the present invention are typically pyrazine diuretics such as amiloride, as described in U.S. Pat. No. 4,501,729 (applicant specifically intends the disclosure of this and all other patent references cited herein to be incorporated herein by reference in their entirety). The term "amiloride" as used herein includes the pharmaceutically acceptable salts thereof, such as (but not limited to) amiloride hydrochloride, as well as the free base of amiloride. The quantity of amiloride included may be an amount sufficient to achieve dissolved concentrations of amiloride on the airway surfaces of the subject of from about $10^{-7}$ to about $10^{-3}$ Moles/liter, and more preferably from about $10^{-6}$ to about $10^{-4}$ Moles/liter.

As noted above, the method of the present invention may also further comprise the step of removing retained mucus secretions from the lungs of the subject prior to the step of administering the lantibiotic. This facilitates application of the active agent to the respiratory epithelia during the administering step. Such removal of retained mucus secretions can be carried out by any suitable means, including postural drainage, antibiotic administration (e.g., intravenous or inhalation administration of cephalosporin or aminoglycoside antibiotics such as Tobramycin), and/or inhalation administration of DNase. In addition, the present invention may be carried out on patients such as children prior to decline of respiratory function (e.g., patients essentially free of lung blockage due to retained mucus secretions). Such patients can be genetically predisposed to becoming afflicted with lung disease (e.g., cystic fibrosis) as hereinbefore described.

The active compounds disclosed herein may be administered to the lungs of a patient by any suitable means, but are preferably administered by generating an aerosol comprised of respirable particles, the respirable particles comprised of the active compound, which particles the subject inhales. The respirable particles may be liquid or solid. The particles may optionally contain other therapeutic ingredients such as a sodium channel blocker as noted above, with the sodium channel blocker included in an amount effective to inhibit the reabsorption of water from airway mucous secretions.

Particles comprised of active compound for practicing the present invention should include particles of respirable size: that is, particles of a size sufficiently small to pass through the mouth and larynx upon inhalation and into the bronchi and alveoli of the lungs. In general, particles ranging from about 0.5 to 10 microns in size (more particularly, less than about 5 microns in size) are respirable. Particles of non-respirable size which are included in the aerosol tend to deposit in the throat and be swallowed, and the quantity of non-respirable particles in the aerosol is preferably minimized. For nasal administration, a particle size in the range of 10–500 μm is preferred to ensure retention in the nasal cavity.

Liquid pharmaceutical compositions of active compound for producing an aerosol can be prepared by combining the active compound with a suitable vehicle, such as sterile pyrogen free water. Other therapeutic compounds, such as a sodium channel blocker, may optionally be included.

Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant which serves to facilitate the formation of an aerosol. A suitable dispersant is lactose, which may be blended with the active compound in any suitable ratio (e.g., a 1 to 1 ratio by weight). Again, other therapeutic compounds, such as amiloride, may also be included.

The dosage of active compound for prophylaxis or treatment of lung disease will vary depending on the condition being treated and the state of the subject, but generally may be an amount sufficient to achieve dissolved concentrations of active compound on the airway surfaces of the subject of from about $10^{-9}$ to $10^{-3}$ Moles/liter, and more preferably from $10^{-7}$ to $10^{-5}$ Moles/liter. Depending on the solubility of the particular formulation of active compound administered, the daily dose may be divided among one or several unit dose administrations. Preferably, the daily dose is a single unit dose, which is preferably administered from 1 to 3 times a week. Treatments may continue week to week on a chronic basis as necessary (i.e., the active agent can be administered chronically). Administration of the active compounds may be carried out therapeutically (i.e., as a rescue treatment) or prophylactically, but preferably the compounds are administered prophylactically, either before substantial lung blockage due to retained mucus secretions has occured, or at a time when such retained secretions have been at least in part removed, as discussed above.

Aerosols of liquid particles comprising the active compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. the carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 μ, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

The present invention also encompasses a method of treating infection by *M. tuberculosis* (e.g., slowing or inhibiting the growth thereof or killing the bacteria), particularly drug resistant strains of *M. tuberculosis* (e.g., strains resistant to treatment with streptomycin, isoniazid, rifampin, ethambutol, or pyrazinamide) (see generally W. Jacobs et al., *Science* 260, 819 (7 May 1993); M. Baringa, New Test Catches Drug-Resistant TB in the Spotlight, *Science* 260, 750 (7 May 1993); T. Frieden, *New Engl. J. Med.* 328, 521 (25 Feb. 1993)) and multiple drug resistant strains of *M. tuberculosis* (e.g., strains resistant to treatment with two or more of streptomycin, isoniazid, rifampin, ethambutol, or pyrazinamide), using lantibiotics. Lantibiotics suitable for use in the present invention include, but are not limited to, duramycin, nisin, subtilin, epidermin, Pep 5, gallidermin, mersacidin, actagardine, cinnamycin, and ancovenin, or the pharmaceutically acceptable salt thereof, as discussed above. Duramycin and the pharmaceutically acceptable salts thereof are particularly preferred. The tuberculosis infection may be in the lung of the subject being treated, or may be an extrapulmonary infection such as of the pleura, lymphatic system, bone, genito-urinary tract, cerebral meninges, central nervous system, peritoneum, or skin.

Pharmaceutical compositions for use in the present method of treating tuberculosis include those suitable for inhalation, oral, rectal, topical, (including buccal, sublingual, dermal and intraocular) parenteral (including subcutaneous, intradermal, intramuscular, intravenous and intraarticular) and transdermal administration. Inhalation therapy is discussed above. The compositions may conveniently be presented in unit dosage form and may be prepared by any of the methods well known in the art. The most suitable route of administration in any given case may depend upon the anatomic location of the *M. tuberculosis* infection in the subject, the nature and severity of the condition being treated, and the particular active compound which is being used. The formulations may conveniently be presented in unit dosage form and may be prepared by any of the methods well known in the art.

In the present method of treating *M. tuberculosis*, the lantibiotics are administered in a dose of from 1 to 100 mg/kg per day. The dose of active agent will vary according to the condition being treated and the dose at which adverse pharmacological effects occur. One skilled in the art will take such factors into account when determining dosage.

The present method of treating tuberculosis is concerned primarily with the treatment of human subjects but may also be employed for the treatment of other mammalian subjects, such as dogs, cats and cows, for veterinary purposes.

In one embodiment of the present invention, aerosolized duramycin is administered to the lungs of a subject with pulmonary tuberculosis, in an amount sufficient to achieve dissolved concentrations of duramycin on the airway surfaces of the subject of from $10^{-7}$ to $10^{-3}$ Moles/liter. In another embodiment of the present invention, duramycin is administered by an intravenous bolus or by infusion, most preferably by infusion, in a dose range of from 70 mg/day to 2.5 g/day, and more preferably in a dose range of from 150 mg/day to 2 g/day.

Lantibiotics used in the present method of treating tuberculosis may be administered in conjunction with another anti-tubercular agent, such other anti-tubercular agents including, but not limited to, ethambutol, streptomycin, isoniazid, rifampin, and pyrazinamide. These additional anti-tubercular agents may be administered in a manner and in an amount in accordance with conventional techniques. See generally Goodman and Gilman's The Pharmacological Basis of Therapeutics, 1210–1212 (Seventh Ed. 1985).

In a further aspect of the present invention, lantibiotics may be used alone or in combination with one or more anti-tubercular agents for the prophylaxis or treatment of tuberculosis.

In the manufacture of a medicament according to the invention (a "formulation"), active agents or the physiologically acceptable salts thereof (the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 99% by weight of the active compound. One or more active compounds may be incorporated in the formulations of the invention (e.g., the formulation may contain one or more additional anti-tubercular agents as noted above), which formulations may be prepared by any of the well known techniques of pharmacy consisting essentially of admixing the components, optionally including one or more accessory therapeutic ingredients.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations for oral administration may optionally include enteric coatings known in the art to prevent degradation of the formulation in the stomach and provide release of the drug in the small intestine.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, e.g., *Pharmaceutical Research* 3, 318 (1986)) and typically take the form of an optionally buffered aqueous solution of the active compound.

Formulations suitable for inhalation administration comprise a lantibiotic and optionally one or more additional anti-tuberculosis agents prepared as discussed above. Means for inhalation administration are as discussed above.

The following examples are provided to more fully illustrate the present invention and should not be construed as restrictive thereof. In the following examples, CF means cystic fibrosis, cm means centimeter, cc means cubic centimeter, kg means kilogram, ml means milliliter, M means molar, µM means micromolar, µg means microgram, µA means microampere, $ED_{50}$ means the dose which produces the desired effect in 50% of test animals, and temperatures are given in degrees centigrade unless otherwise indicated.

EXAMPLE 1

Effect of Duramycin on Chloride Conductance and Calcium Metabolism In Vitro

In vitro investigations were conducted employing primary cultures of normal and Cystic Fibrosis (CF) airway epithelium grown on collagen supports in defined medium to show the effect of duramycin on chloride conductance and calcium metabolism.

1. Ussing Chamber Studies

The $Cl^-$ secretory response to stimulation of normal and CF airway epithelium was studied under short circuit ($I_{sc}$) conditions employing tissues mounted in Ussing chambers. Ussing chambers are well known in the art and the manner of their use in the present example would be readily apparent to one skilled in the art.

Tissues were first treated with amiloride to remove the $Na^+$ current. Normal tissues were defined by demonstrating an increase in current following pretreatment with amiloride and subsequent treatment with forskolin (10 µM). The resulting increase in $I_{sc}$ under these conditions has been established as a $Cl^-$ secretory response. In normal tissues and employing this protocol, subsequent use of duramycin at a dose of $10^{-6}$M induced a dramatic increase in the $Cl^-$ current, raising the $I_{sc}$ from a baseline of 20 µA/cm² after amiloride treatment to a peak of 50 µA/cm². (Data not shown.)

Primary cultures of normal tissues were treated with $10^{-6}$M duramycin employing three different bathing solutions in the Ussing chambers: control solution containing both $Na^+$ and $Cl^-$, solution without $Na^+$, and solution without $Cl^-$. The tissues in both the control and $Na^+$ free conditions responded by increasing the $I_{sc}$ after stimulation with duramycin. (Data not shown.) The tissue in the $Cl^-$ free condition, however, showed a markedly attenuated response to duramycin. These observations further support the conclusion that duramycin induces a $Cl^-$ secretory response in primary cultures of human airway epithelia.

The $Cl^-$ secretory response to duramycin is characterized by a relatively sustained increase in $I_{sc}$ lasting in some instances longer than 1 hour. This is in contrast to the response to other agonists such as ATP, which produce a rapid onset of action and a rapid return to the baseline current.

Duramycin-treated normal tissues demonstrated an increase in $I_{sc}$ when subsequently stimulated with ATP and forskolin. (Data not shown.) The tissues' ability to respond to these agents after duramycin treatment demonstrates that the tissues were not significantly damaged by duramycin.

2. Dose Response Study

A dose response study established that the maximal response to duramycin was achieved at $10^{-6}$M with an $ED_{50}$ of $3\times10^{-7}$M. Resistance across the tissue began to fall at doses of about $2\times10^{-6}$M. The fall in resistance was interpreted as an indication of toxicity.

3. Cl⁻ Response in Normal and CF Tissue

Seven normal and five CF tissues were studied, as above, employing duramycin at a concentration of $10^{-6}$M. These studies confirmed that a significant Cl⁻ secretory response secondary to stimulation with duramycin could be produced in both normal and CF tissues. The Cl⁻ secretory response in CF tissue (i.e., the change in $I_{sc}$) was approximately twice that seen in normal tissue. (Data not shown).

4. Mechanisms of Action

Preliminary studies were also done investigating possible mechanisms of action. Employing positive controls, these studies were performed in a CF human transformed cell line, CFT43, to evaluate whether the tissue generated cAMP in response to duramycin stimulation. The studies demonstrated that duramycin stimulation did not cause intracellular cAMP levels to rise (data not shown). Employing the same cell line, further studies were performed to determine if the duramycin effect was mediated by the stimulation of phospholipase C (PLC) and the generation of inositol phosphates (IPs). There were no detectable amounts of IPs produced in response to stimulation with duramycin (data not shown).

The in vitro studies described above indicate that (1) increases in $I_{sc}$ in response to duramycin were secondary to Cl⁻ ion movement across the tissue; and (2) duramycin stimulates a Cl⁻ secretory current in both normal and CF tissues in vitro. Preliminary studies of the mechanism of action of duramycin suggest that neither cAMP nor PLC is involved.

EXAMPLE 2

In Vivo Efficacy Animal Model

1. The Animal Model

The model developed employed 30 kg male dogs that were anesthetized with intravenous pentobarbital and maintained on a intravenous infusion of normal saline at 75 cc/hour. The dogs were intubated. Ventilatory support was provided by a Harvard™ piston pump. Adequate ventilation and oxygenation were documented by arterial blood gas studies. Peak airway pressures (PAP) were measured and continuous monitoring of hemoglobin saturation was accomplished by pulse oximetry. The model allowed the animal to be absolutely stationary during the study, allowed ventilatory status of the animal to be fixed and set at a physiological state, provided the opportunity for prolonged study of the animal should this prove to be necessary, and standardized the amount of stress the animals experienced.

Drug and vehicle were delivered through the endotracheal tube. The drug was nebulized employing a Pulmo-Aid™ Compressor and a DeVilbiss™ nebulizer. The drug (50 µM; 3 ml) in a saline vehicle or the saline vehicle alone (control) was nebulized for 6 minutes during which 0.7 ml thereof was delivered to the animal. Based on previous work, it was established that the concentration of duramycin achieved in the airway was about $3\times10^{-7}$M, the estimated $ED_{50}$. After 6 minutes, a clean and dry nebulizer was exchanged for the test nebulizer containing the drug or vehicle. The investigators were blinded as to whether drug or vehicle was given.

2. Measurements of airway fluid

Airway liquid measurements were made by applying dry preweighed filter paper to the cartilaginous portions of the airway for 20 seconds. This was accomplished employing transbronchial biopsy forceps to grasp the papers. The forceps and papers were stored in plastic catheters. Sampling the airway liquid was accomplished by first inserting the bronchoscope through the endotracheal tube. Care was taken not to allow contact between mucosa and the bronchoscope. The catheter containing the biopsy forceps and filter papers was introduced into the airway lumen through the channel in the bronchoscope. The biopsy forceps were then pushed out of the catheter and the filter papers gently applied to the mucosa. After 20 seconds the biopsy forceps and filter papers were pulled back into the catheter and removed through the bronchoscope for weighing. The filter papers were accessed for weighing by again pushing the forceps holding the filter paper out of the catheter. In order to account for evaporative losses from the filter papers when exposed to room air, the time required to place the papers on the scales and perform the initial weighing was recorded. Three subsequent weighings over time were then made. A regression line was calculated. The weight of the filter papers at time zero, that is when they were maximally wet, was defined as the time when the filter papers were pushed out of the catheter after having been applied to the airway mucosa. The amount of fluid on the filter paper was taken as the difference between the dry weight of the papers and their weight at time zero. Each set of samples to be compared were further corrected for differences in the initial weight of the dry filter papers.

3. Protocols

Two protocols were ultimately employed to accomplish the evaluation of the duramycin's effects on fluid transport. The goal of the first protocol was to study the effects on airway surfaces liquid of (1) repeatedly sampling the airway, and (2) nebulizing the normal saline vehicle. These issues were of concern in studying the duration of action of duramycin since previous studies employing the awake sheep model demonstrated a marked secretory response in the airway after four samples had been obtained, and demonstrated a 35% increase in surface liquid after delivery of vehicle.

Protocol 1 required, immediately prior to conducting the test studies, weighing and loading the filter papers into catheters. Ten separate catheter-forceps-filter paper set-ups were available. Ten measurements of airway liquid were then made in different areas of the trachea over a thirty-minute period, with measurements made at three minute intervals. The catheters were then reloaded and the saline vehicle nebulized onto the airway. Ten more measurements of airway surface liquid were then made over another thirty minute period.

Protocol 2 required sampling the airway every four minutes to obtain 30 measurements of airway liquid. This required reloading the 10 catheters twice during each experiment. Each reloading required 20 minutes. This protocol allowed the airway to be sampled over 160 minutes. Drug and vehicle administration were separated by one week in any one animal. Protocol 2 was employed to compare the effects of duramycin versus vehicle.

EXAMPLE 3

Results of In Vivo Efficiency Studies

Sampling the canine trachea ten times every three minutes (Protocol 1, above) did not significantly alter the amount of fluid recovered (data not shown). Further, there was no difference between the amount of liquid recovered from the trachea in the canine model at baseline and that recovered after nebulization of the normal saline vehicle. FIG. 1.

Initial studies employing Protocol 1 to study the effects of duramycin on the airway demonstrated that duramycin caused a marked and sustained increase in the amount of fluid recovered from the airway. After duramycin was administered the amount of airway fluid received did not return to baseline during the 30 minute measurement period. Protocol 1 thus did not allow a control comparison if the duramycin was given first, since the airway surface liquid did not return to baseline even two hours following its administration.

Figure 2:
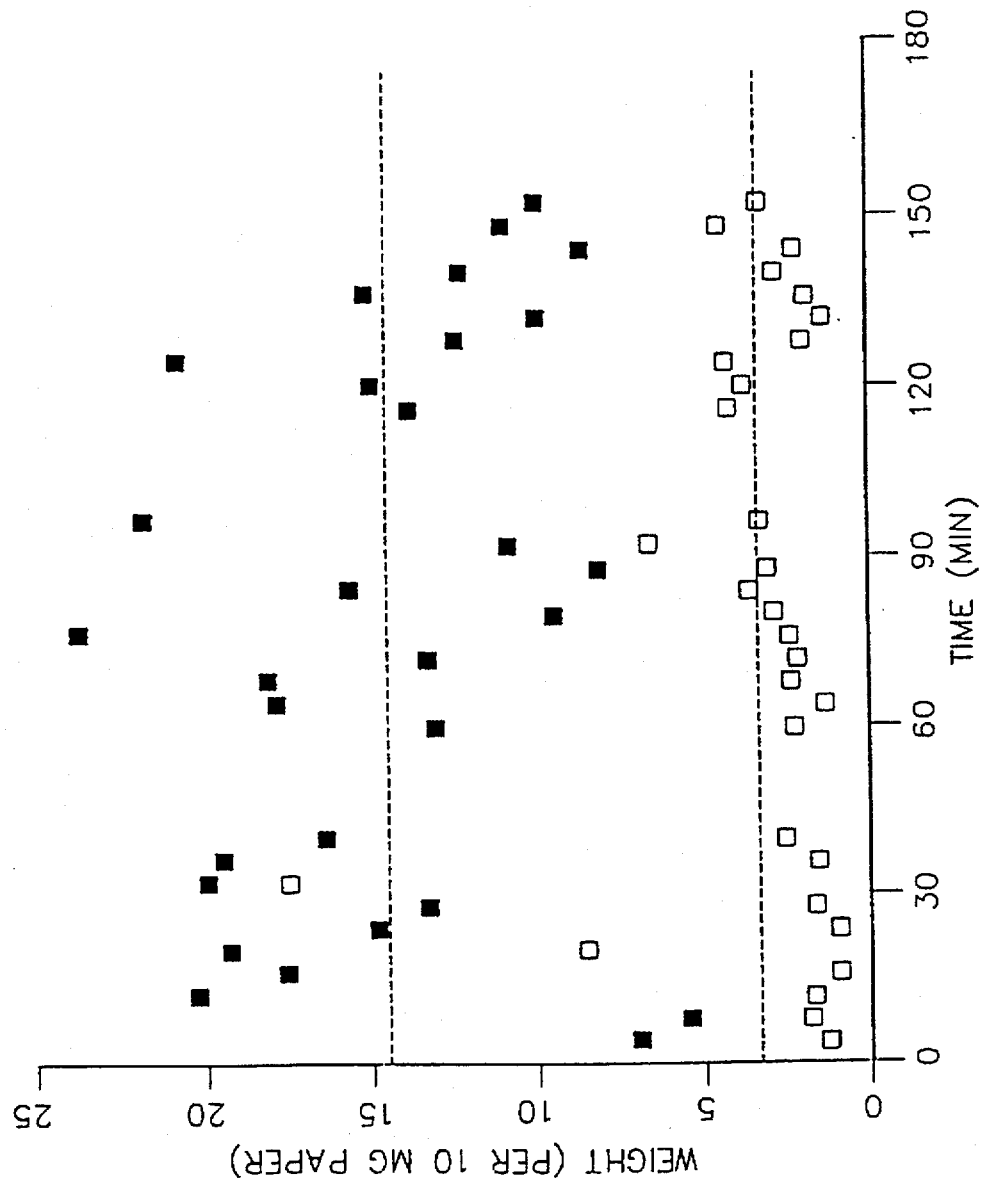
FIG. 2 is a graph of the weight of filter paper samples taken from canine trachea over a 160 minute interval following administration of either duramycin or saline control. Animals treated first with vehicle and then with duramycin one week later demonstrated a stable baseline over 160 minutes. Open boxes are saline treatments; filled boxes are duramycin treatments.
Figure 3:
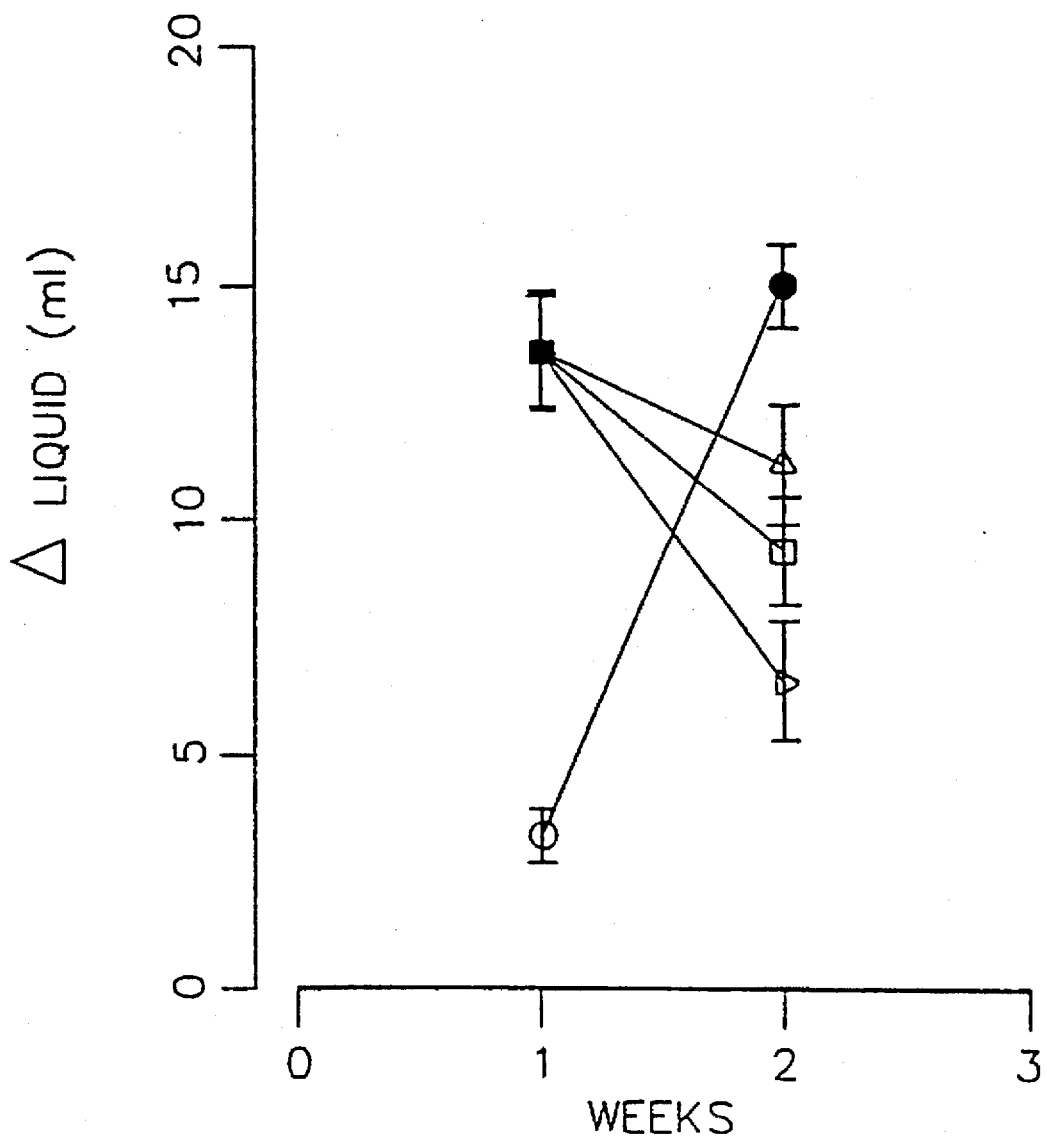
FIG. 3 is a graph comparing the amount of surface airway liquid recovered from the canine trachea model after administration of saline vehicle followed by administration of duramycin one week later, and the amount of surface airway liquid recovered from the canine trachea model after administration of duramycin followed by administration of saline vehicle one week later. Filled symbols are duramycin treatments; open symbols are vehicle treatments; each symbol (circle, square, triangle with point up, triangle with point right) represents a different animal.
Figure 4:
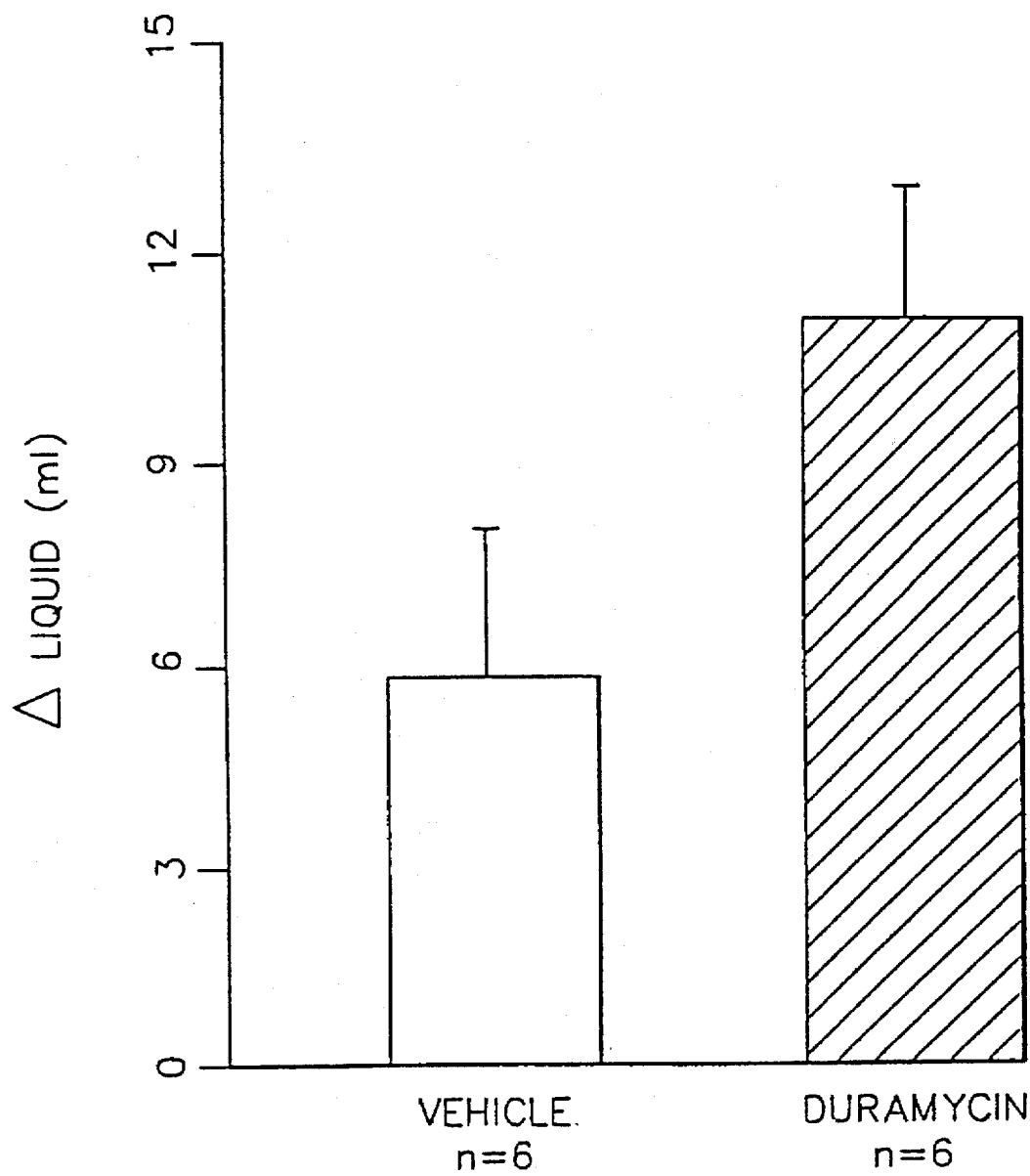
FIG. 4 is a graph comparing the amount of airway surface liquid recovered from the canine trachea model after duramycin treatment and after vehicle control treatment. Open box is vehicle; cross-hatched box is duramycin treatment; n=6 in each group.

In an attempt to deal with this unexpectedly long duration of drug action, the 160 minute Protocol 2 was developed, which includes separating the administration of drug and vehicle by one week. Animals treated first with vehicle and then duramycin one week later demonstrated a stable baseline over 160 minutes. FIG. 2. Further, a several-fold increase in the amount of fluid recovered over baseline after duramycin administration was observed. Sustained plateaus without a significant slope were demonstrated for fluid measurements after vehicle and after duramycin. Because there was no trend in the data suggesting a flooding or drying of the airway, the values for the amount of surface liquid were averaged to produce a single value for duramycin and vehicle in each animal. This protocol too, however, was limited due to the fact that one week following administration of duramycin, surface airway liquid measurements after vehicle administration remained elevated as shown in FIG. 3. Therefore, only studies where vehicle was administered first were employed to compare the effects of duramycin to vehicle. Compared to the vehicle controls, these studies demonstrated a significant (p=0.0179 (paired); p=0.0335 (unpaired)) increase in the amount of airway surface liquid recovered after duramycin treatment of the airway (FIG. 4). On average, duramycin produced a doubling of the amount of fluid recovered. This compared to the approximate 50% increase noted in the sheep model after amiloride treatment. W. Mentz et al., *Am. Rev. Resp. Dis.* 134, 938–943 (1986).

EXAMPLE 4

Effect of Duramycin on *M. tuberculosis* Strains In Vitro

The effects of duramycin on the growth of three recent clinical isolates of multidrug resistant *Mycobacterium tuberculosis* and one laboratory strain of *M. tuberculosis* was assayed using the BACTEC™ 460 TB (Becton Dickinson, Towson, Md.) system. The BACTEC™ 460 TB system is an automated apparatus that assays the growth of microorganisms; the system is known in the art and its use has been established in numerous clinical trials and cooperative studies. In the automated assay, a growth medium (7H12 broth obtained from Becton Dickinson, Towson, Md.) containing $^{14}C$-labeled palmitic acid as a single source of carbon is placed in multiple 4 ml vials. Each vial is injected with dilutions of the drug or drugs being studied, and inoculated with 0.1 ml of bacterial suspension from an actively growing BACTEC™ vial. Subsequent growth of the organisms leads to the metabolism of the substrate, with release of $^{14}CO_2$ into the sealed vial which is then measured by the BACTEC™ 460 instrument. The data is expressed as a "growth index" (GI) on a scale from 0 to 1000. Test vials are read every day for 12 days and the growth curve plotted (GI vs. day).

In the present experiment, each of three drug resistant strains of *M. tuberculosis*, and a drug-sensitive laboratory strain of *M. tuberculosis* was tested against duramycin (100 µM, 10 µM, 1 µM, and 0.1 µM) and against four traditional anti-tuberculosis drugs: streptomycin (6 µg/ml), isoniazid (0.2 µg/ml), rifampin (2 µg/ml), and ethambutol (7.5 µg/ml).

*M. tuberculosis* 57778

Figure 5:
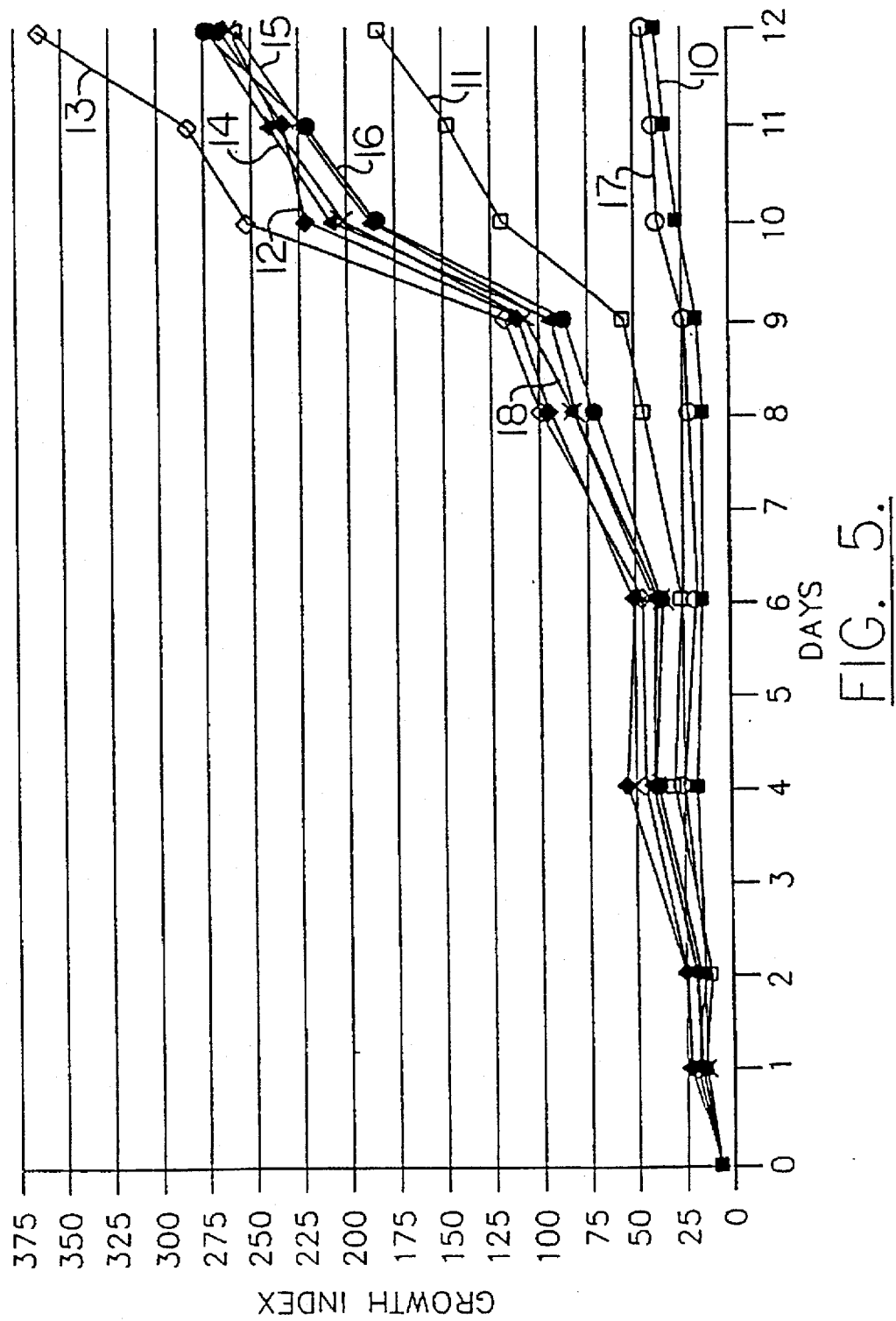
FIG. 5 is a graph comparing the growth of *Mycobacterium tuberculosis* 57778 over 12 days in cultures containing duramycin 100 µM (filled box; line 10), duramycin 10 µM (filled box; line 11), duramycin 1.0 µM (filled diamond, line 12), duramycin 0.1 µM (filled diamond, line 13), streptomycin 6 µg/ml (filled triangle; line 14), isoniazid 0.2 µg/ml (open triangle; line 15), rifampin 2 µg/ml (filled circle; line 16), ethambutol 7.5 µg/ml (filled circle; line 17), or no drug ("x"; line 18). This strain is streptomycin (S), isoniazid (I), and rifampin (R) resistant, but ethambutol (E) sensitive.

*M. tuberculosis* 57778 is a recent clinical isolate obtained from a New York City Hospital; this strain is resistant to streptomycin, isoniazid, and rifampin, and sensitive to ethambutol. FIG. 5 plots the growth curves for *M. tuberculosis* 57778, as described above, and indicates that 100 µM duramycin is equally as effective as ethambutol against this ethambutol-sensitive strain of *M. tuberculosis*.

*M. tuberculosis* 63169

Figure 6:
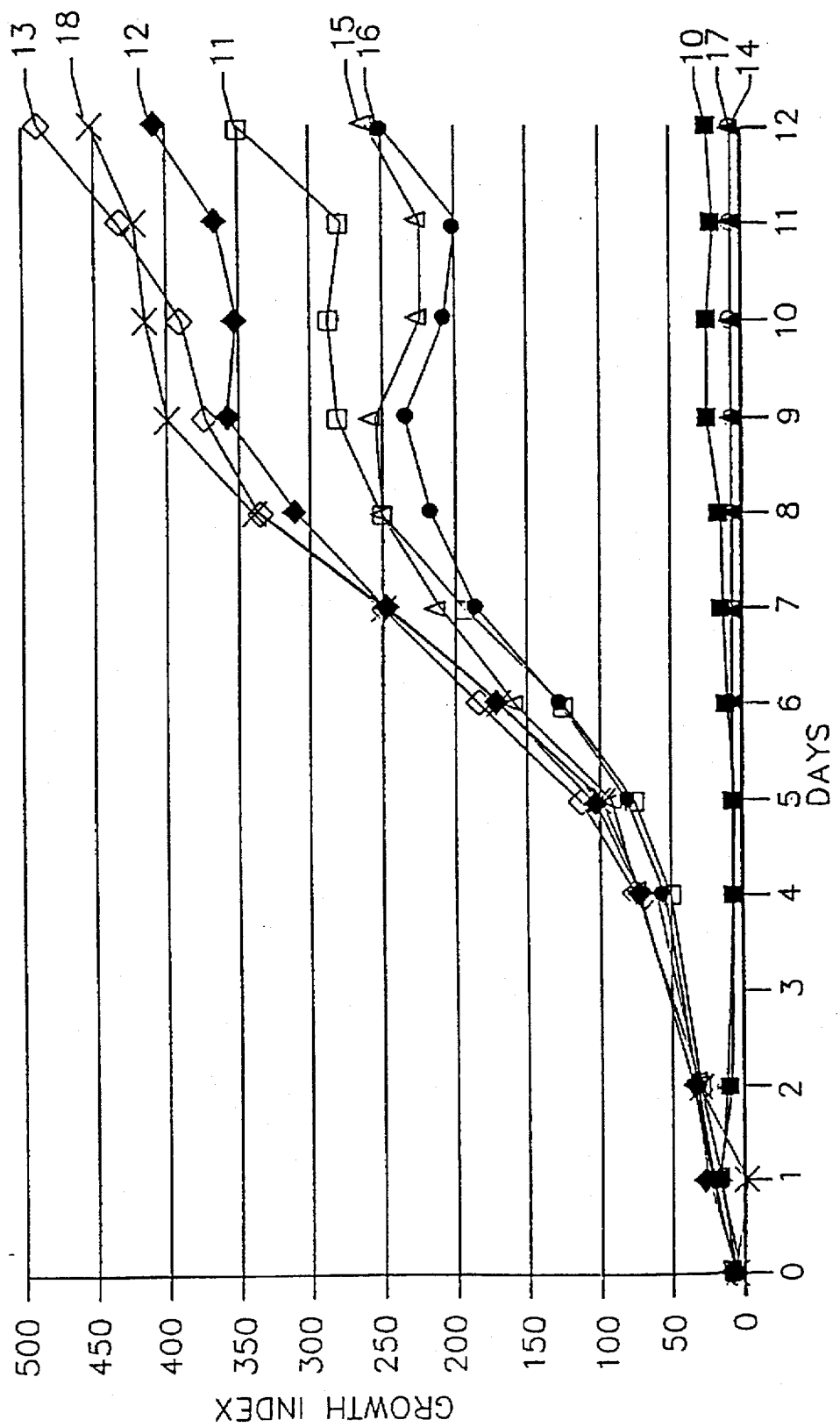
FIG. 6 is a graph comparing the growth of *Mycobacterium tuberculosis* 63169 in cultures over twelve days containing duramycin 100 µM, duramycin 10 duramycin 1.0 µM, duramycin 0.1 µM, streptomycin 6 µg/ml, isoniazid 0.2 µg/ml, rifampin 2 µg/ml, ethambutol 7.5 µg/ml, or no drug. Symbols and abbreviations are as given in connection with FIG. 5 above.

*M. tuberculosis* 63169 is another recent clinical isolate obtained from a New York City Hospital; this strain is resistant to isoniazid and rifampin, and sensitive to streptomycin and ethambutol. FIG. 6 plots the growth curve for *M. tuberculosis* 63169 as described above, and indicates that 100 µM duramycin has activity against this strain approximately equal to that of the two drugs now known to be effective against this strain (streptomycin and ethambutol).

*M. tuberculosis* 65021

Figure 7:
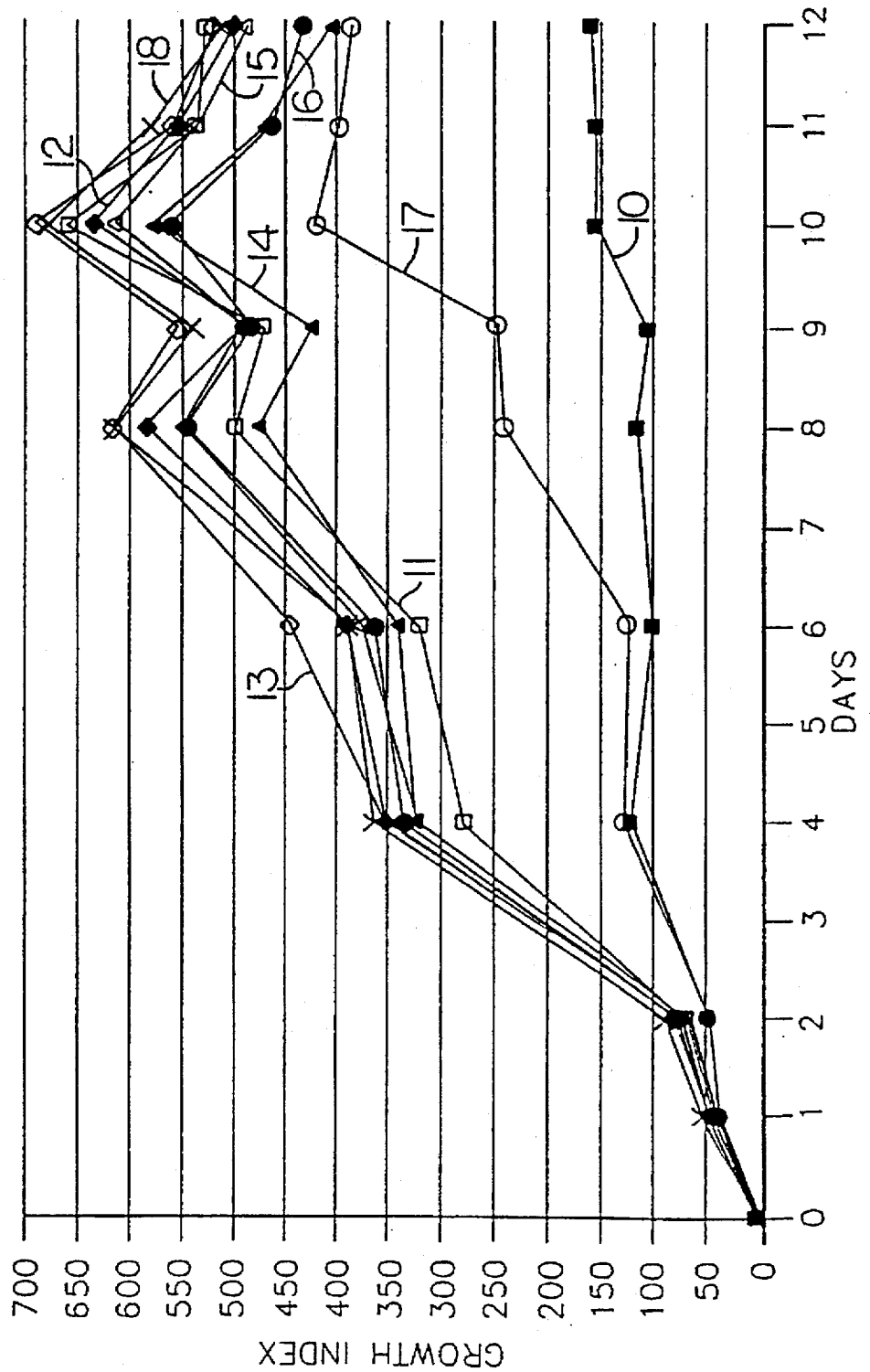
FIG. 7 is a graph comparing the growth of *Mycobacterium tuberculosis* 65021 in cultures over twelve days containing duramycin 100 µM, duramycin 10 µM, duramycin 1.0 µM, duramycin 0.1 µM, streptomycin 6 µg/ml, isoniazid 0.2 µg/ml, rifampin 2 µg/ml, ethambutol 7.5 µg/ml, or no drug. Symbols and abbreviations are as given in connection with FIG. 5 above.

*M. tuberculosis* 65021 is another recent clinical isolate obtained from a New York City Hospital; this strain is resistant to streptomycin, isoniazid and rifampin, and partially resistant to ethambutol. FIG. 7 plots the growth curve for *M. tuberculosis* 65021 as described above, and indicates that 100 µM duramycin shows significantly more activity against this strain than any of the four traditional anti-tuberculosis drugs tested.

*M. tuberculosis* Drug Sensitive Laboratory Strain

Figure 8:
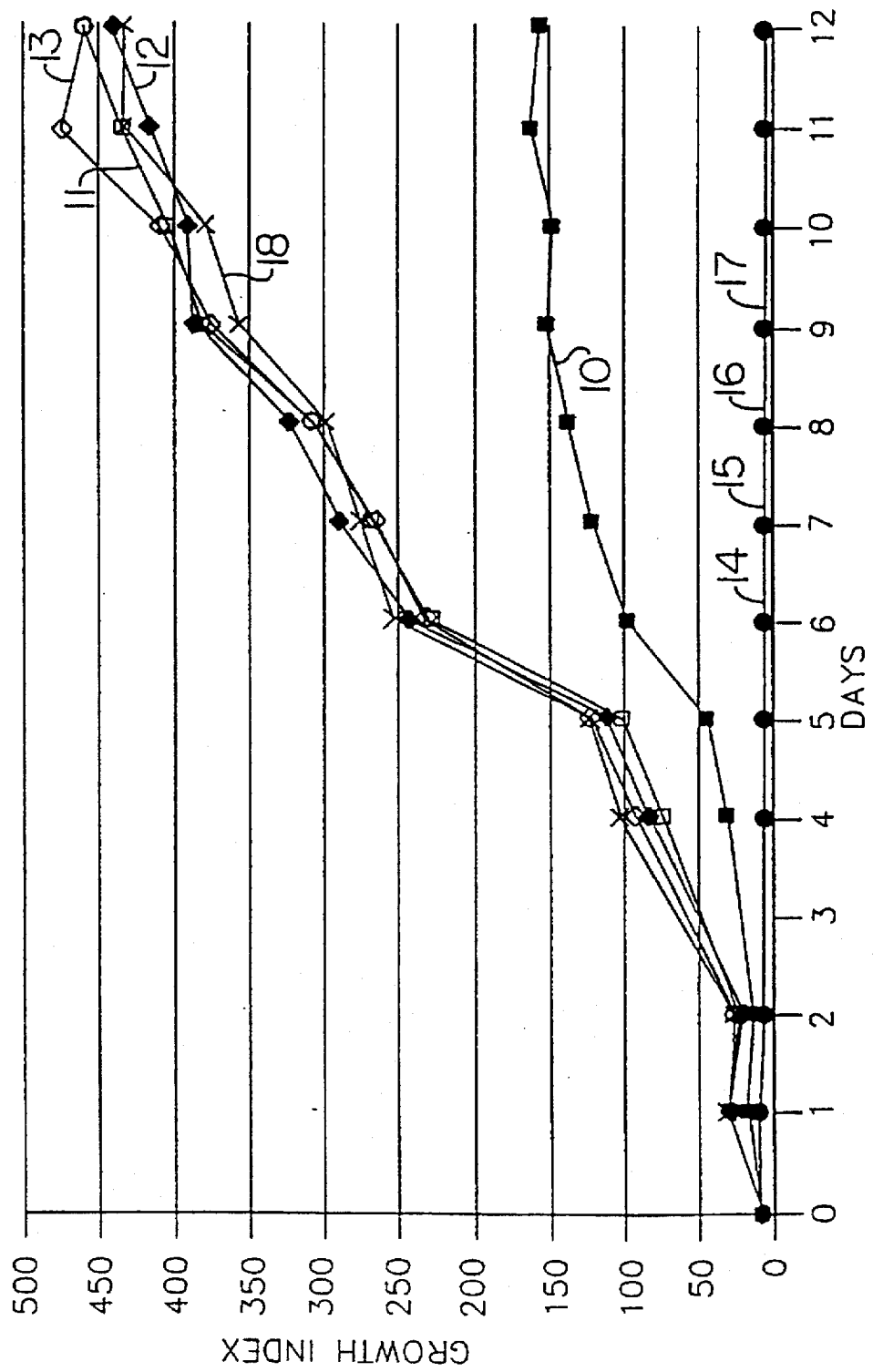
FIG. 8 is a graph comparing the growth of drug-sensitive *Mycobacterium tuberculosis* in cultures over twelve days containing duramycin 100 µM, duramycin 10 µM, duramycin 1.0 µM, duramycin 0.1 µM, streptomycin 6 µg/ml, isoniazid 0.2 µg/ml, rifampin 2 µg/ml, ethambutol 7.5 µg/ml, or no drug. Symbols and abbreviations are as given in connection with FIG. 5 above.

*M. tuberculosis* (drug-sensitive laboratory strain) is sensitive to each of streptomycin, isoniazid rifampin, and ethambutol. FIG. 8 plots the growth curve for *M. tuberculosis* (drug-sensitive laboratory strain) as described above, and indicates that 100 µM duramycin is less active in vitro than streptomycin, isoniazid, rifampin, or ethambutol against this sensitive strain.

The foregoing examples are illustrative of the present invention, and are not to be construed as limiting thereof. The invention is defined by the following claims, with equivalents of the claims to be included therein.

That which is claimed is:

1. A method of combatting *Mycobacterium tuberculosis* infection in a subject in need of such treatment, comprising administering to the lungs of the subject a lantibiotic or a pharmaceutically acceptable salt thereof in an amount effective to combat *M. tuberculosis* infection,
   wherein said subject is afflicted with a drug resistant strain of *M. tuberculosis:*
   wherein said lantibiotic is delivered by administering an aerosol of respirable particles containing said lantibiotic to said subject;
   wherein said aerosol is comprised of particles having a particle size within the range of from about 0.5 to 10 microns;
   wherein said lantibiotic is administered in an amount sufficient to achieve concentrations of said lantibiotic on the airway surfaces of said subject of from about $10^{-9}$ moles/liter to about $10^{-3}$ moles/liter; and wherein said lantibiotic is selected from the group consisting of duramycin, nisin, subtilin, epidermin, Pep 5, gallidermin, mersacidin, actagardine, cinnamycin, and ancovenin.

2. A method according to claim 1, wherein said particles are selected from the group consisting of solid particles and liquid particles.

3. A method according to claim 1, wherein said lantibiotic is administered in an amount sufficient to achieve concentrations of lantibiotic on the airway surfaces of said subject of from about $10^{-8}$ moles/liter to about $10^{-5}$ moles/liter.

4. A method according to claim 1, wherein said lantibiotic is duramycin.

5. A method according to claim 1, wherein said *Mycobacterium tuberculosis* is a multiple drug resistant strain of *M. tuberculosis*.

6. A method according to claim 1, further comprising concurrently administering to said subject an anti-tubercular agent in an amount effective to combat *Mycobacterium tuberculosis* infection.

7. A method according to claim 1, further comprising concurrently administering to said subject an anti-tubercular agent selected from the group consisting of rifampin, streptomycin, isoniazid, ethambutol, and pyrazinamide, said anti-tubercular agent administered in an amount effective to combat *Mycobacterium tuberculosis* infection.

* * * * *